United States Patent [19]

Pool

[11] Patent Number: 4,619,258
[45] Date of Patent: Oct. 28, 1986

[54] ELECTROSURGICAL PENCIL PROVIDING BLADE ISOLATION

[75] Inventor: L. Franklin Pool, Vancouver, Wash.

[73] Assignee: Dart Industries Inc., Northbrook, Ill.

[21] Appl. No.: 585,565

[22] Filed: Mar. 2, 1984

[51] Int. Cl.$^4$ ............................................. A61B 17/39
[52] U.S. Cl. ........................... 128/303.14; 128/303.17; 200/157; 200/159 B
[58] Field of Search ...................... 128/303.13, 303.14, 128/303.17, 303.18, 303.19, 800; 219/234, 240; 200/157, 159 B

[56] References Cited

U.S. PATENT DOCUMENTS

| | | | |
|---|---|---|---|
| 3,801,766 | 4/1975 | Morrison, Jr. | 200/157 |
| 3,911,241 | 10/1975 | Jarrard | 200/157 |
| 4,032,738 | 6/1977 | Esty et al. | 200/157 |
| 4,034,761 | 7/1977 | Prater et al. | 128/303.14 |
| 4,071,028 | 1/1978 | Perkins | 128/303.14 |
| 4,112,950 | 9/1978 | Pike | 128/303.14 |
| 4,123,673 | 10/1978 | Gonser | 128/303.14 |
| 4,170,234 | 10/1979 | Graham | 128/303.14 |
| 4,171,700 | 10/1979 | Farin | 128/303.14 |
| 4,244,371 | 1/1981 | Farin | 128/303.14 |
| 4,343,973 | 8/1982 | Main | 200/159 B |
| 4,349,712 | 9/1982 | Michalski | 200/159 B |
| 4,409,450 | 10/1983 | Blades | 200/159 B |
| 4,427,006 | 1/1984 | Nottke | 128/303.14 |
| 4,443,935 | 4/1984 | Zamba et al. | 128/303.17 X |

FOREIGN PATENT DOCUMENTS

| | | |
|---|---|---|
| 129018 | 7/1932 | Fed. Rep. of Germany ........................ 128/303.17 |
| 614727 | 5/1935 | Fed. Rep. of Germany ...... 200/157 |

OTHER PUBLICATIONS

Knickerbocker, "ESU Safety and the Clinical Engineer: . . . ", in Medical Instrumentation, vol. 14, No. 5, Sep.-Oct. 1980, pp. 257-260.

Primary Examiner—Lee S. Cohen
Attorney, Agent, or Firm—Lee, Smith & Zickert

[57] ABSTRACT

The present invention is comprised of an electrosurgical pencil of the type where current is provided from an electrosurgical generator to the blade of the pencil through a hot lead whenever a switching circuit is activated by interconnecting the hot lead with a switching lead which also runs from the pencil to the generator. The pencil isolates the hot lead from the blade at all times when the switching circuit is not also activated by that pencil. Accordingly, when the generator is caused to transmit current by the activation of one pencil, the current will not reach the blade of other pencils connected to the same generator.

7 Claims, 6 Drawing Figures

ELECTROSURGICAL PENCIL PROVIDING BLADE ISOLATION

BACKGROUND OF THE INVENTION

This invention relates to an electrosurgical pencil and in particular to such a pencil where the hot lead through which current is transmitted to the blade is isolated from the blade until that particular pencil has been activated.

It is well known in the prior art to use high frequency current to perform surgical functions. In this type of equipment an electrosurgical generator generates current in a particular wave form upon demand and this current is carried to an electrosurgical pencil having a small blade. The current then is transmitted through the blade to the patient and back to the generator through a ground plate attached to the patient. Since the blade is quite small relative to the ground plate, the energy being transferred to the patient through the blade is concentrated on a small area where the high frequency oscillations cause tissue destruction. Typically such devices have two modes of operation, cutting and coagulation, which require current having different wave forms.

In these devices the current is initiated and interrupted by means of a switching circuit in the generator which is controlled either by a switch in the pencil or by a floor switch. In the former, a switching lead runs from the generator to the pencil, with the switching circuit in the generator being activated to provide current to the hot lead when the switching lead and hot lead are electrically interconnected at the pencil. Thus there are three leads to the pencil; a hot lead which runs from the generator to the blade and two switching leads which run from the generator to the pencil. Located in the pencil is a three-position switch which in one position connects one of the switching leads to the hot lead, thereby providing cutting current to the blade, in a second position connects the other switching lead to the hot lead, thereby providing coagulating current to the blade, and in a third position electrically separates all of the leads from one another thereby providing no current to the blade.

The difficulty with these units lies in the fact that several surgeons often simultaneously use pencils which are connected to a common generator. Since the generator provides current upon activation of the switching circuit, when one pencil is activated current is supplied to all of them. Thus, when one of the pencils is left in a position where the blade comes in contact with the patient, and the other pencil is activated, either intentionally or by accident, the first pencil will cause a burn to occur in the patient. While attempts have been made to design the switching circuit in the generator to provide safeguards which present current from accidentally flowing to the wrong pencil, heretofore no safeguards have been provided in the pencil itself to prevent this from occurring.

SUMMARY OF THE INVENTION

The foregoing shortcomings of the prior art electrosurgical pencils are overcome in the present invention by providing a switch in the pencil having a case with two cylindrical cavities and two slots which extend along its length and through the cavities. Located in one of the slots and extending through both of the cavities is a hot lead which receives current from an electrosurgical generator to which it is connected. Two switching leads, which also are connected to the generator, are located in the other slot. The switching leads are electrically isolated from one another and one extends through each of the cavities. The cavities have larger diameter counterbores in their upper portions with the bottoms of the counterbores being located above the bottoms of the cavities by a distance which is greater than the diameter of the leads.

Located in the cavities are deformable conductive domes having diameters approximately equal to the diameter of the counterbores. Thus, the domes are located in the counterbores where their peripheries are above the leads, and therefore not in contact with them. However, when the domes are deflected their center portions do make contact with the leads. Accordingly, by deflecting one of the domes the switching lead associated with that cavity is brought into contact with the hot lead which activates the switching circuit in the generator and causes it to transmit current through the hot lead.

Mounted on the top of the case is a thin flexible element which is electrically conductive on the side facing the domes and electrically non-conductive on the other side. Non-conductive sleeves fit in the cavity between the domes and the flexible element to keep them separated from one another. The flexible element is electrically connected to the blade of the electrosurgical pencil. Thus when the flexible element is deflected into the cavity sufficiently to deflect the dome into contact with the leads, the hot lead and the blade also become electrically interconnected. Due to the elasticity of the dome and the flexible element when the latter is released, both resume their relaxed positions and electrical contact is broken both between the hot lead and the switching lead, and between the hot lead and the blade. Since the only way that current from the generator can reach the blade is upon deflection of the flexible element in the pencil carrying that blade, when the generator is caused to generate current by activation of one of several pencils, the current does not flow through to the blade of any of the other pencils.

A rocker switch located on the electrosurgical pencil has prongs which deflect the flexible element into contact with one of the domes when it is rocked in either direction. Thus, cutting current is provided when the rocker plate is rocked in one direction, and coagulating current is provided when it is rocked in the other direction, and no current is provided when it is released.

The foregoing objectives, features and advantages of the present invention will be more readily understood upon consideration of the following detailed description of the invention taken in conjunction with the accompanying drawings.

DETAILED DESCRIPTION OF THE INVENTION

Figure 1:
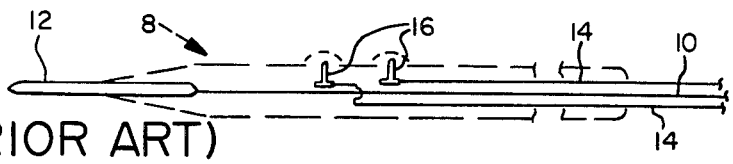
FIG. 1 is a schematic view showing the electrical circuitry of an electrosurgical pencil of the prior art type.

Referring first to the schematic of FIG. 1, a typical prior art electrosurgical pencil 8 provides a hot lead 10 which runs uninterrupted from the generator which provides current to it (not shown), to the blade 12. Current flows through the hot lead 10 to the blade whenever it is supplied by the generator, which occurs, among other times, when a switching circuit in the generator is engaged by electrically connecting one of the switching lines 14 to the hot lead by depressing the appropriate switch 16.

Figure 2:
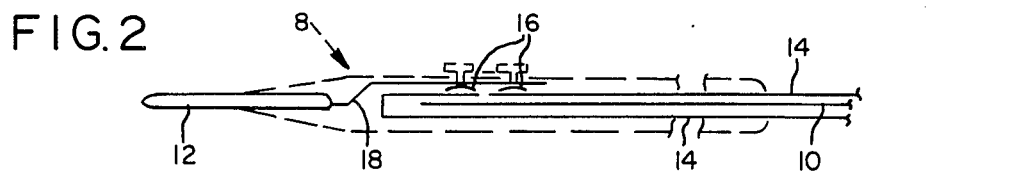
FIG. 2 is a schematic view showing the electrical circuitry of the pencil of the present invention.

With the present invention on the other hand, shown schematically in FIG. 2, the hot lead does not extend uninterrupted from the generator to the blade, but instead the blade normally is isolated electrically from the hot lead. Thus the lead 18 from the blade is only connected to the hot lead 10 when one of the switch 16 is activated to complete the switching circuit.

Figure 4:
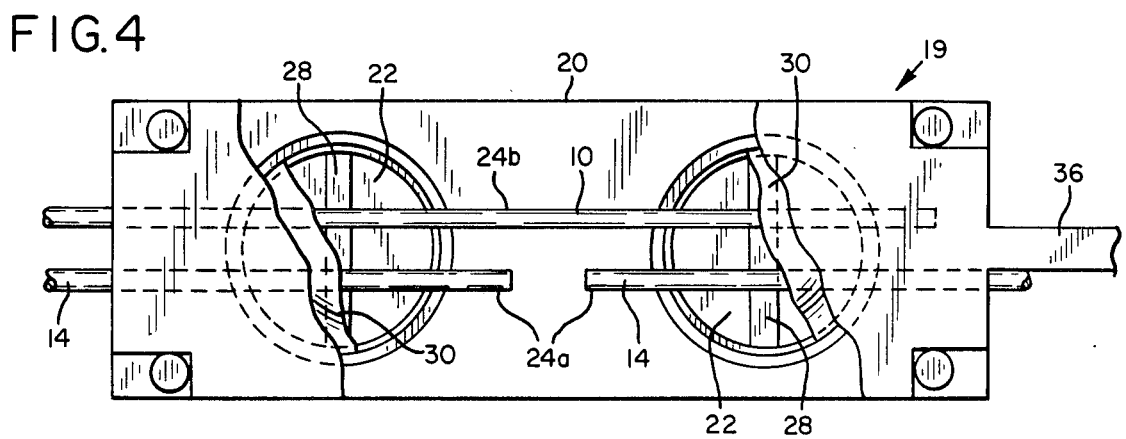
FIG. 4 is an enlarged plan view, partially broken away to show hidden detail, of a switch which is a component of the present invention.
Figure 5:
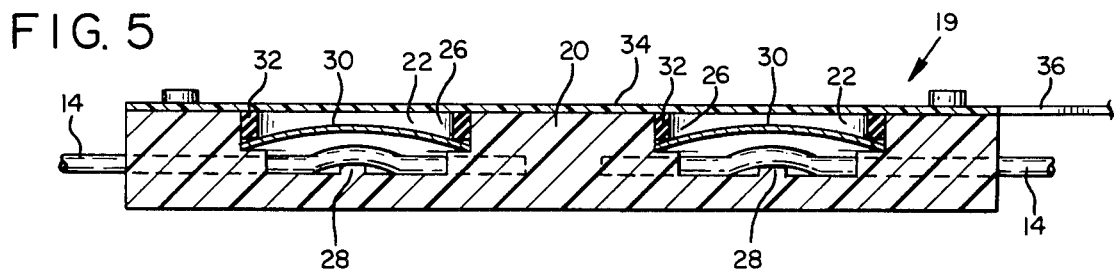
FIG. 5 is a sectional view, taken on the line 5—5 of FIG. 4, showing the switch in its open position.
Figure 6:
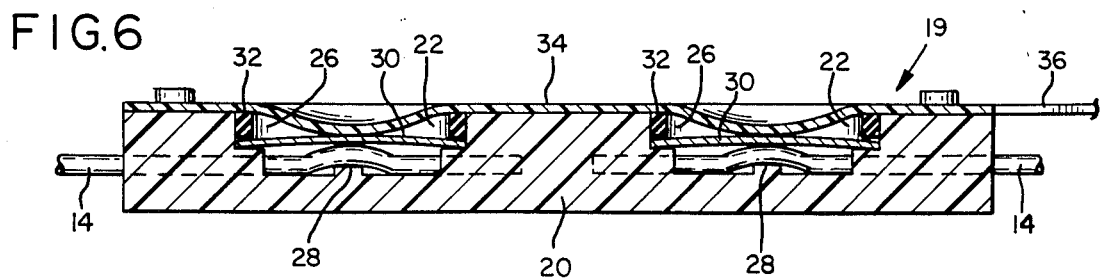
FIG. 6 is a cross-sectional view, similar to FIG. 5, showing the switch in its closed position.

In the preferred embodiment, the switch 19 comprises a case 20, shown in detail in FIGS. 4, 5 and 6, which carries the operative elements of the switch. Located in the case 20 are two cylindrical cavities 22 and two slots 24a and 24b which extend along their length through the cavities, with the bottoms of the slots having the same depth as the bottoms of the cavities. In the embodiment illustrated neither of the slots 24a or 24b extends completely across the case. The slot 24a is interrupted for a short distance intermediate the cavities, and the other slot 24b terminates short of one end of the case. Neither of these interruptions of the slots is necessary, but, as will be seen later, they facilitate assembly of the switch.

The slot 24b, which extends uninterrupted from one end of the case through both of the cavities 22 has the hot lead 10 positioned in it. One of the switching leads 14 is located in one of the slots 24a and the other switching lead 14 is located in the other slot 24a. Thus the hot lead extends through both cavities and out one end of the case and each switching lead extends through only one of the cavities and out of the end of the case in which that cavity is located.

The cavities 22 have larger diameter counterbores 26 which terminate slightly more than the diameter of the leads 10 and 14 above the bottoms of the cavities. Ridges 28 which extend across the bottoms of the cavities have a height which is slightly greater than the difference between the diameter of the leads and the height of the counterbores 26. Thus the tops of the leads are below the bottoms of the counterbores where they enter the cavities and above the bottoms of the counterbores where they cross the ridges 28.

Located in each of the cavities is an electrically conductive deformable dome 30, of the type commonly used in printed circuit board dome switches, which has a diameter substantially equal to the diameter of the counterbore 26. Due to the relative heights of the counterbores and the leads, neither of the domes is in contact with the leads when it is in its relaxed position, FIG. 5, but, due to the ridge 28, each dome does make contact with the leads when it is deflected, FIG. 6. Thus, when either of the domes 30 is deflected, the switching lead entering the cavity carrying that dome is connected with the hot lead, thereby causing the generator to provide current through the hot lead. A non-conductive cylindrical sleeve 32 fits above each dome to retain it at the bottom of the counterbore.

Figure 3:
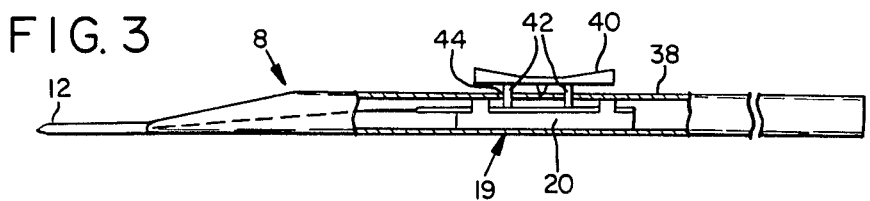
FIG. 3 is a side elevational view, partly broken away, showing the pencil of the present invention.

Attached to the top of the case 20 is a thin flexible element 34 which is electrically conductive on the side facing the case and electrically non-conductive on the other side. A thin tab 36 on the element 34 extends outwardly from the case on the end which is opposite the end which receives the hot lead 10. Referring to FIG. 3, this tab 36 is electrically connected to the blade 12 through the lead 18. Thus the hot lead remains electrically isolated from the blade until the flexible element is deflected into contact with one of the domes 30 and that dome is deflected into contact with the hot lead 10. When this occurs current flows through the hot lead 10, the dome 30, the element 34 and the lead 18 to the blade 12, FIG. 6. The electrical circuit, which extends through the patient, is completed by means of a ground connection (not shown) between the patient and the generator.

The case is installed into the electrosurgical pencil 38, FIG. 3, and the device which activates the switch is attached to the outside of the case to complete the assembly. In the embodiment illustrated the activation device comprises a rocker plate 40 which has a pair of prongs 42 extending from it, one being located above each of the domes 30. The rocker plate is rotatably attached to the pencil with the prongs extending through openings 44 in the pencil in a manner such that when the rocker plate is centered, neither dome is deflected and when it is rocked towards either end the prong on that end causes the element 34 to be deflected into contact with one of the domes 30 and the dome to be deflected into contact with the leads 10 and 14. When the rocker plate is released, the resilience of the dome causes it to be recentered and the element 34 and dome 30 return to their relaxed positions. Since the element 34 is separated from the domes by the non-conductive washers 32 the domes remain at the bottom of the counterbores 26 and the element remains separated from them except when it is deflected upon contact by one of the prongs of the rocker plate.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. In an electrosurgical pencil of the type having a pencil housing, a blade at an end of the housing which receives current through a hot lead from an electrosurgical current generator upon electrical interconnection of a switching lead extending between the generator and the pencil with the hot lead, the improvement comprising: said pencil including
   (a) first switch means for making and breaking contact between said switching lead and said hot lead;
   (b) second switch for making and breaking contact between said hot lead and said blade; and
   (c) means for preventing contact in said first switch means unless there is also contact in said second switch means.

2. The improvement of claim 1 wherein there are multiple first switch means each having a different switching lead and all having a common hot lead.

3. The improvement of claim 1 wherein said first and second switch means are normally open.

4. The improvement of claim 1 wherein said first swtich means comprises a deformable, electrically conductive dome including activation means for positioning said dome in either a relaxed position, where said first switch means is open, or a deflected position, where said first switch means is closed.

5. In an electrosurgical pencil of the type having a pencil housing, a blade at an end of the housing, a hot lead for carrying current from an electrosurgical generator through the housing to the blade, first and second switching leads for carrying activation signals from the pencil to the electrosurfical generator, and a switch carried by the housing for activating the electrosurgical generator by making selective electrical connection between the first switching lead and the hot lead or the second switching lead and the hot lead, the improvement comprising:

said switch including means for isolating said blade from said hot lead when said switch is not activated and for connecting said blade to said hot lead when said switch is activated.

6. In an electrosurgical pencil of the type having a pencil housing, a blade at one end of the housing which receives current through a hot lead from an electrosurgical generator upon electrical interconnection of a switching lead extending between the generator and the pencil with the hot lead, the improvement comprising:

first switch means for making and breaking contact between said switching lead and said hot lead, said first switch means comprising a deformable, electrically conductive dome including activation means for positioning said dome in either a relaxed position, where said first switch means is open, or a deflected position, where said first switch means is closed; and second switch means for making and breaking contact between said hot lead and said blade, said second switch means comprising a deformable conductive element which is interposed between said dome and said activation means, such that it makes contact with said dome when said dome is positioned in its deflected position by said activation means and does not make contact with said dome when it is not being positioned in its deflected position by said activation means, said conductive element being electrically connected to said blade.

7. The improveemnt of claim 6 wherein there are two of said first switch means each comprising a deformable, electrically conductive dome, and two of said swtich means each comprising respective portions of said deformable conductive element, and wherein said activation means comprises a rocket plate having a pair of prongs depending therefrom disposed above the respective domes of each said first switch means and above the respective portions of said deformable conductive element, one of said prongs causing deflection of one of said portions of the deformable conductive element and the dome of one of said first switch means when said rocker plate is rocked in one direction, and the other of said prongs causing deflection of the other of said portions of the deformable conductive element and the dome of the other frist switch means when the rocker plate is rocked in the other direction.

* * * * *